(12) United States Patent
Zimmermann et al.

(10) Patent No.: US 9,181,353 B2
(45) Date of Patent: Nov. 10, 2015

(54) METHOD FOR MANUFACTURING HYDROXYETHYL STARCH DERIVATIVES

(75) Inventors: Werner Zimmermann, Bernburg (DE); Jan Lukowczyk, Halle / Saale (DE)

(73) Assignee: Serumwerk Bernburg AG, Bernburg, Saale (DE)

( * ) Notice: Subject to any disclaimer, the term of this patent is extended or adjusted under 35 U.S.C. 154(b) by 20 days.

(21) Appl. No.: 14/127,766

(22) PCT Filed: Jun. 21, 2012

(86) PCT No.: PCT/EP2012/061958
§ 371 (c)(1),
(2), (4) Date: Dec. 19, 2013

(87) PCT Pub. No.: WO2012/175608
PCT Pub. Date: Dec. 27, 2012

(65) Prior Publication Data
US 2014/0128594 A1    May 8, 2014

(30) Foreign Application Priority Data

Jun. 21, 2011   (EP) ..................................... 11170761

(51) Int. Cl.
| | | |
|---|---|---|
| *C08B 31/18* | (2006.01) | |
| *C08B 31/10* | (2006.01) | |
| *A61K 47/48* | (2006.01) | |
| *C08B 31/12* | (2006.01) | |

(52) U.S. Cl.
CPC ............. *C08B 31/10* (2013.01); *A61K 47/4823* (2013.01); *C08B 31/12* (2013.01); *C08B 31/185* (2013.01)

(58) Field of Classification Search
None
See application file for complete search history.

(56) References Cited

U.S. PATENT DOCUMENTS

| | | |
|---|---|---|
| 3,639,588 A | 2/1972 | Alsop et al. |
| 2008/0207562 A1 | 8/2008 | Zander et al. |

FOREIGN PATENT DOCUMENTS

| | | |
|---|---|---|
| CN | 101262889 A | 9/2008 |

OTHER PUBLICATIONS

N. Ternes, et al., Iron availability and complex stability of iron hydroxyethyl starch and iron dextran—a comparative in vitro study with liver cells and macrophages, Nephrology Dialysis Transplantation 22 (Jun. 7, 2007), 2824-2830.

*Primary Examiner* — Layla Bland
(74) *Attorney, Agent, or Firm* — The Webb Law Firm

(57) ABSTRACT

A method for manufacturing a modified hydroxyethyl starch carrying a heptonic acid residue on at least one of its termini is disclosed. Within this method, the following steps are carried out: a) dissolving hydroxyethyl starch in water, b) adjusting the pH value to a value of 8.0 to 10.0, c) adding a cyanide compound to the hydroxyethyl starch solution, heating the solution to a temperature of 80 to 99° C. and keeping it at this temperature for a first time period, and d) adjusting the pH value to a value of 2.0 to 4.0, bringing the solution to a temperature of 50 to 90° C. and keeping it at this temperature for a second time period.

19 Claims, 1 Drawing Sheet

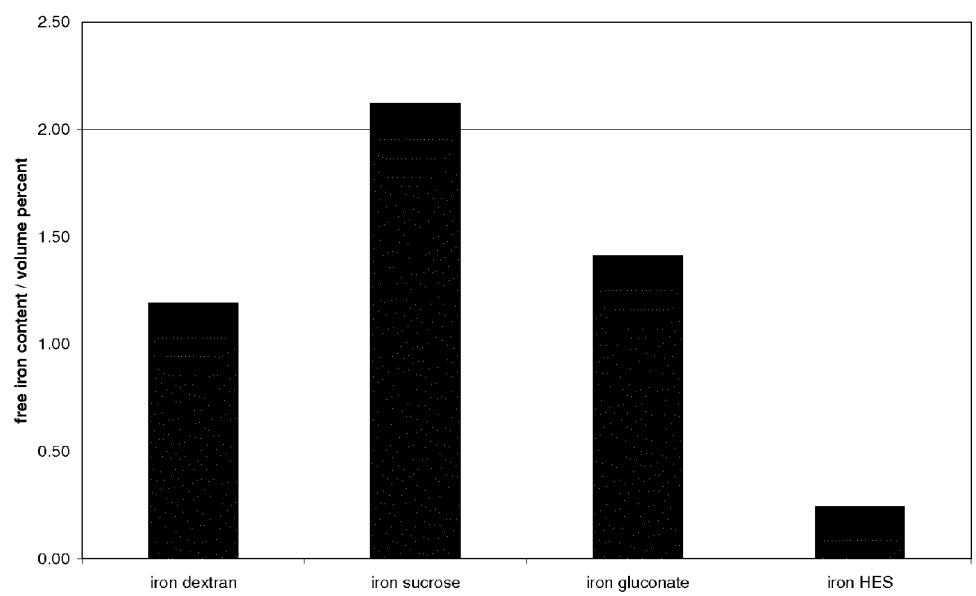

METHOD FOR MANUFACTURING HYDROXYETHYL STARCH DERIVATIVES

CROSS-REFERENCE TO RELATED APPLICATIONS

This application is a national phase patent application of International Application No. PCT/EP2012/061958, filed on Jun. 21, 2012, which claims priority of European Patent Application No. 11170761.8, filed on Jun. 21, 2011, the disclosures of which are hereby incorporated in their entirety by reference.

BACKGROUND OF THE INVENTION

The invention relates in an aspect to a method for manufacturing a hydroxyethyl starch derivatives.

Patients suffering from end-stage renal disease under chronic haemodialysis often show iron deficiency anaemia. This is based on the fact that the application of recombinant human erythropoietin in haemodialysis results in an enhanced iron requirement which cannot be satisfied by intestinal iron absorption. Therefore, iron supplementation is necessary to support an erythropoiesis initiated by erythropoietin therapy to counteract renal anaemia.

There exist several formulations for administering iron to patients. These formulations are usually complexes of iron ions with polymeric carbohydrates like dextran or organic compounds like sucrose or gluconate to form polynuclear complexes with metal ions.

In particular, dextran complexing iron has been used in the past to treat iron deficiency anaemia. However, such dextrans have comparatively many side effects and can show an anaphylactic effect, because anti-streptococci antibodies can react onto dextrans.

Ternes et al.: "Iron availability and complex stability of iron hydroxyethyl starch and iron dextran—a comparative in vitro study with liver cells and macrophages", Nephrology Dialysis Transplantation 22 (2007), 2824-2830 described the use of hydroxyethyl starch as carrier for iron ions. However, no suited manufacturing method by which high amounts of hydroxyethyl starch can be produced in a reliable manner has been published so far.

SUMMARY OF THE INVENTION

It is an object of an aspect of the present invention to provide a method for producing hydroxyethyl starch derivatives being suited as carrier for metal ions.

This object is achieved by a method comprising the following steps:
a) First, hydroxyethyl starch is dissolved in water.
b) Then, the pH value is adjusted to a value of 8.0 to 10.0
c) Afterwards, a cyanide compound is added t the hydroxyethyl starch solution. Then the solution is heated to a temperature of 80 to 99° C. and kept at this temperature for a first time period.
d) Finally, the pH value is adjusted to a value of 2.0 to 4.0 and the solution is brought to a temperature of 50 to 90° C. and kept at this temperature for a second time period.

A starch manufactured by this method is characterized in that it carries a heptonic acid residue on at least one of its termini. Thus, such starch might carry a number of heptonic acid residues per molecule, depending on the number of terminal glucosyl residues being present in the starch molecule. This heptonic acid residue increases the hydrophilicity of the hydroxyethyl starch and increases the stability of complexes formed by this hydroxyethyl starch with ligands, like for example metal ions such as iron ions.

Speaking more generally, hydroxyethyl starch (HES) is a starch in which some of the hydroxyl groups of the single glucosyl residues are substituted by a hydroxyethyl residue. An exemplary excerpt of a structure of hydroxyethyl starch is depicted in the following formula:

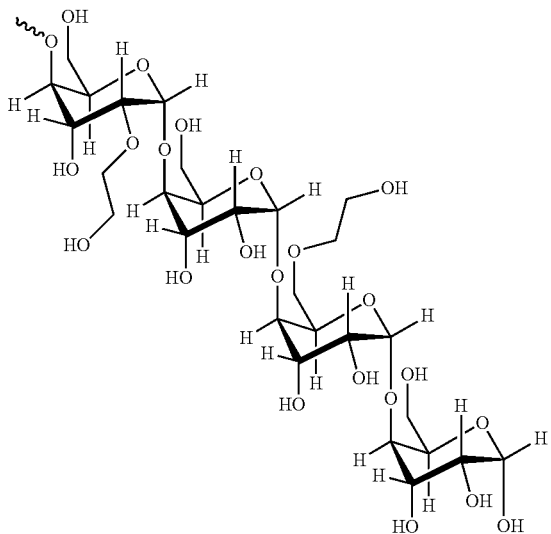

The amount of hydroxyethyl residues (in the present case two hydroxyethyl residues per four glucosyl residues of the starch) is to be understood only exemplarily. In the formula depicted above, only 1,4-alpha glycosidic bonds between the single glucosyl residues are shown. However, as is well known by a person skilled in the art, the starch comprises also 1,6-alpha glycosidic bonds leading to branching of the starch and increasing the number of terminal glucosyl residues in the starch molecule.

If one terminus of the hydroxyethyl starch is modified by a heptonic acid residue, the according modified starch (which carries one heptonic acid residue) can be depicted as follows:

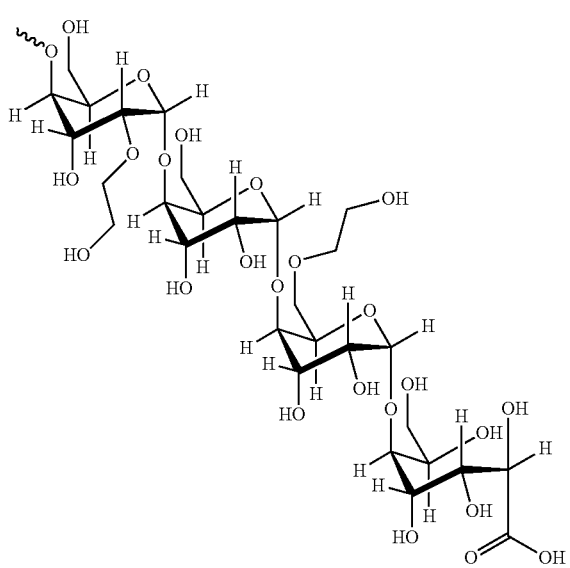

The modification by the heptonic acid residue takes place by converting the terminal glucosyl residue of the hydroxyethyl starch into a heptonic acid residue. The specific reaction scheme will be explained later on in more detail.

In an embodiment, the hydroxyethyl starch used in the method has a weight average molecular weight (Mw) of less than 200 000 g/mol, in particular of less than 130 000 g/mol, in particular of less than 100 000 g/mol, in particular of less than 90 000 g/mol, in particular of less than 80 000 g/mol and very particular of less than 75 000 g/mol. A very well suited molecular weight is in the range of 55 000 g/mol to 85 000 g/mol. Such a hydroxyethyl starch has a comparatively lower molecular weight than (non-modified) hydroxyethyl starches used in the medical field at present. A suited method for determining the molecular weight of the hydroxyethyl starch is size exclusion chromatography (SEC).

In an embodiment, the hydroxyethyl starch has an average degree of molar substitution of 0.4 to 0.6, in particular of 0.45 to 0.55. An average degree of molar substitution of around 0.50 is particularly well suited. The average degree of molar substitution is a measure for the amount of hydroxyl groups being substituted by a hydroxyethyl residue per glucosyl residue. Since each glucose unit (or glucosyl residue) bears three hydroxyl groups, the average degree of molar substitution can be three at the maximum. An average degree of molar substitution of 0.5 indicates that (on an average or statistic basis) in each second glucosyl residue one hydroxyl group is substituted by a hydroxyethyl residue.

In an embodiment, the hydroxyethyl starch has a weight average molecular weight of 55 000 to 85 000 g/mol, in particular around 70 000 g/mol, and an average degree of molar substitution of 0.45 to 0.55, in particular around 0.50. Such a hydroxyethyl starch with a molecular weight of 70 000 g/mol±15 000 g/mol and an average degree of molar substitution of 0.5±0.05 can also be referred to as HES 70/0.5.

Generally, hydroxyethyl starch can have different organic origins. For example, hydroxyethyl starch can be produced starting from waxy corn starch. However, in an embodiment, potato starch is used as starting material for the production of hydroxyethyl starch which is then further modified to contain at least one heptonic acid residue. Waxy corn starch and potato starch differ in their molar constitution with respect to the amount of 1,4-alpha glycosidic bonds and 1,6-alpha glycosidic bonds.

The reactions taking place during the before-mentioned reaction steps a) to d) will now be explained in more detail. First, it should be noted that the glucose residues of the hydroxyethyl starch are present in two tautomeric forms, namely in a cyclic hemiacetal form (shown in the following reaction scheme on the left) and in an open aldehyde form (shown in the following reaction scheme on the right):

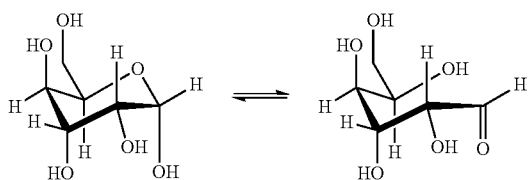

The aldehyde group of such a glucosyl residue can react with a cyanide group of a cyanide compound to form a novel C—C single bond. By reducing the pH value, a saponification of the nitrile group takes place. The result of this reaction is the introduction of a carboxyl group into the existing molecule. The according reaction scheme is depicted in the following:

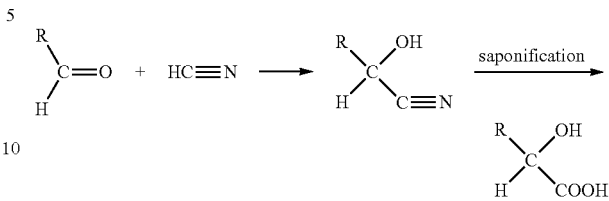

In an embodiment, the hydroxyethyl starch is dissolved in water having a high level of purity, like e.g. highly pure water, ultra pure water or water for injection, in step a). In a further embodiment, the starch is dissolved to reach a concentration of 12.0 to 20.0° Bx. The measurement unit ° Bx (degree Brix) is a unit representative of the sugar content of an aqueous solution. This unit is well known to a person skilled of the art. 1° Bx corresponds to 1 g of sucrose in 100 g of solution. Thus, 1° Bx corresponds to 1 percent by weight (w/w) of sucrose. Also in case of starch like hydroxyethyl starch a 1:1 conversion of ° Bx to percent by weight can be done. Thus, a hydroxyethyl starch solution having a concentration of 1% (w/w) has a starch concentration of 1° Bx. Consequently, 12.0 to 20.0° Bx correspond to 12.0 to 20.0% (w/w) hydroxyethyl starch.

In an embodiment, the concentration is in the range of 13.0 to 19.0° Bx and particularly in a concentration range of 14.0 to 18.0° Bx.

In an embodiment, the pH value is adjusted in step b) to a value of 8.5 to 9.5. Sodium lye (an aqueous solution of sodium hydroxide) is well suited for this pH adjustment.

In an embodiment, sodium cyanide is used as a cyanide compound in step c). In a further embodiment, the solution is heated to a temperature of 83 to 95° C. and particularly to a temperature of 86 to 92° C. When keeping the solution at this temperature, for the first time period, it is aerated in an embodiment. This reaction step is also referred to as alkaline heat treatment. In an embodiment, the first time period is 3 to 8 hours, in particular 4 to 7 hours and in particular approximately 5 hours long.

In step d), the pH value is adjusted to a value of 2.5 to 3.5 in an embodiment. Hydrochloric acid is a well suited acid for this pH adjustment. In an embodiment, the solution is brought in step d) to a temperature of 60 to 80° C. In an embodiment, the solution is aerated while it is kept at this temperature for the second time period. This reaction step is also referred to as acid heat treatment. In an embodiment, the second time period is 10 to 16 hours long, in particular 12 to 14 hours.

As already indicated above, the heptonic acid modified hydroxyethyl starch is well used as a carrier for metal ions which can be complexed by the modified hydroxyethyl starch in a very well suited manner. This is particular true if the metal ions are iron ions. Thus, in an embodiment, the hydroxyethyl starch is complexed with iron ions. Such a complex of iron ions within modified hydroxyethyl starch is a suited carrier to provide iron to a human or animal body. In this respect, the modified hydroxyethyl starch produced according to an aspect of the invention is a well suited carrier molecule for metal ions like iron ions.

To manufacture such a complex, method step d) is, in an embodiment, succeeded by further method steps explained in the following:

a) The solution is cooled down to a temperature of 10 to 40° C.

b) An iron compound is added to the solution.

c) The pH value of the solution is adjusted to a value of 2.0 to 4.0 after a third time period has passed after the iron compound addition.

d) Finally, the complex of hydroxyethyl starch and the iron compound is stabilized by at least one heat treatment. This heat treatment is performed by heating the solution to a temperature of 80 to 99° C., cooling it down to a temperature of 10 to 40° C. and then adjusting the pH value to a value of 3.0 to 7.0.

In an embodiment, the solution is cooled down in step e) and/or h) to a temperature of 15 to 35° C., in particular of 20 to 30° C.

In a further embodiment, the iron compound added in step f) is an iron salt. In doing so, iron ions are particularly well accessible to a form a complex with the hydroxyethyl starch.

In an embodiment, the metal ions are present in the complex in an amount of 1% (w/w) to 20% (w/w), in particular of 2% (w/w) to 15% (w/w), in particular of 3% (w/w) to 10% (w/w), in particular of 4% (w/w) to 6% (w/w), in particular around 5% (w/w), in each case with respect to the total weight of the complex of hydroxyethyl starch and metal ions.

In an embodiment, the iron ions are ions of ferric iron, i.e. iron(III) ions. They have an oxidation number of +3 and can also be written as $Fe^{3+}$ ions. Ferric ions can be provided by, e.g., ferric salts, ferric oxide or ferric hydroxide. Other ferric compounds known per se to a person skilled in the art are of course also suited for providing ferric ions. Thus, in an embodiment, the iron salt is an iron(III) salt.

In a further embodiment, the complex of hydroxyethyl starch and iron ions has a radius of gyration in the range of approximately 30 to 70 nm, in particular of approximately 40 to 60 nm, in particular of approximately 45 to 55 nm, and very particular of around 50 nm. Thus, the complex has a size which is comparable to that of viruses. The size (or radius of gyration) of the complex can for example be determined by the field-flow fractionation (FFF), in particular if carried out as asymmetric flow FFF. This method is per se known to a person skilled in the art and will not be described here in detail.

A final solution of the complex of hydroxyethyl starch and iron ions has, in an embodiment, a dark brown colour and exhibits a viscosity of less or equal 25 mm²/s, a density of 1.050 to 1.150 g/ml, a pH value of 5.0 to 7.5, a cyanide content of less than 0.1 ppm, a free iron content of less than 0.1 g/100 ml, a chloride content of less than 0.5 g/100 ml, a total iron content of 4.750 to 5.250 g/100 ml, an HES content of 5 to 15 g/100 ml and/or a dry matter content of 10 to 25 g/100 ml.

In an embodiment, not all but only some of the beforementioned criteria are fulfilled, wherein any combination of these parameters is possible.

In a further embodiment, the pH value of the solution is adjusted in step g) to a value of 2.5 to 3.5. This pH adjustment can, for example, be done by a carbonate like for example sodium carbonate, in particular in form of a carbonate solution. In an embodiment the third time period is 12 to 48 hours long, in particular 24 to 36 hours.

In an embodiment, step h) is carried out in such a way that the pH value obtained after a further heating step succeeding a previous heating step is higher than the pH value in the previous heating step.

In a further embodiment, the heat treatment step h) of the method is carried out by performing the following sub-steps:

h1) The solution is heated to temperature of 80 to 99° C., kept at this temperature for a fourth time period, cooled down to temperature of 10 to 40° C. and then the pH value of the solution is adjusted to a value of 3.0 to 5.0.

h2) The solution is afterwards again heated to a temperature of 80 to 99° C., kept at this temperature for a fifth time period, cooled down to a temperature of 10 to 40° C. and then the pH value of the solution is adjusted to a value of 4.0 to 6.0.

h3) Finally, the solution is once again heated to a temperature of 80 to 99° C., kept at this temperature for a sixth time period, cooled down to a temperature of 10 to 40° C. and then the pH value of the solution is adjusted to a value of 5.0 to 7.0.

In carrying out these three subsequent sub-steps h1) to h3), the pH value of the solution is, in an embodiment, increased from step h1) to step h2) to step h3). In an embodiment, the solution is adjusted to a pH value of 3.5 to 4.5 in step h1). In an embodiment, the pH value of the solution is adjusted to a value of 4.5 to 5.5 in step h2). In a further embodiment, the pH value of the solution is adjusted to a value of 5.5 to 6.5 in step h3).

In an embodiment, the temperature to which the solution is heated is in the range of 85 to 95° C. in any of steps h1), h2) and h3), wherein the temperatures in all reaction steps are independent on each other.

In another embodiment, the solution is cooled down to a temperature of 15 to 35° C., in particular of 20 to 30° C. in any of steps h1), h2) and h3), wherein the temperature in all reaction steps are independent on each other.

In an embodiment, the fourth, fifth and sixth time period are each 15 minutes to 3 hours, in particular 30 minutes to 2 hours, in particular 45 minutes to 1.25 hours and very particular around 1 hour long, wherein the duration of each time period is independent on the duration of the other time periods.

Step h), in particular when carried out according to any of the embodiments, is decisive for the structure formation of the generated complex of hydroxyethyl starch and the iron or other metal compound.

In an embodiment, the iron compound to be used to form a complex of the hydroxyethyl starch and the iron is an iron(III) salt. Iron(III) chloride (also known as ferric chloride, $FeCl_3$) is a very well suited ferric salt for this purpose.

To adjust the concentration of the formed solution, the solution can be concentrated until the specified hydroxyethyl starch concentration or iron concentration is reached. If the concentration is already higher than wanted, the formed solution can be diluted. Suited means for dilution are water like for example water for injection.

For adjusting the pH value to the desired value, any base or acid can be used. Sodium hydroxide and hydrochloric acid are very well suited means for adjusting the pH value.

In an embodiment, also the viscosity and/or density of the solution are controlled.

Finally, the solution can be filtered to reduce the amount to germs being present in the solution. Finally, it is filled into appropriate packaging.

The invention relates in an aspect also to the use of hydroxyethyl starch being produced by a method according to the above-mentioned explanations as active ingredient of a medicinal product or medicament. Whereas "normal" hydroxyethyl starch is already being used as active ingredient of a medicinal product (for volume replacement), this is not the case for heptonic-acid modified hydroxyethyl starch.

Furthermore, the invention relates in an aspect to the use of the complex of modified hydroxyethyl starch and iron ions produced by a method according to the above explanations as a medicament for intravenous iron therapy.

Finally, the invention also relates in an aspect to the use of this complex of heptonic-acid modified hydroxyethyl starch and iron ions produced by a method according to the above explanations for the treatment of iron deficiency anaemia.

Hereby, also pharmaceutical compositions containing a hydroxyethyl starch produced by a method according to the preceding explanations, in particular in form of a complex with a metal ion, are disclosed.

BRIEF DESCRIPTION OF THE DRAWINGS

FIG. 1 shows the free iron content of iron HES in comparison to other iron-containing preparations.

DESCRIPTION OF THE INVENTION

Further details of aspects of the invention will be explained in the following examples.

Example 1

Manufacturing of HES Heptonic Acid

For manufacturing heptonic-acid modified hydroxyethyl starch, HES 70/0.5 was dissolved in water for injection to reach a concentration of 14.0 to 18.0° Bx. Then, the pH value was adjusted to a value of 8.5 to 9.5 with sodium lye. For formation of the heptonic acid terminus of the hydroxyethyl starch, sodium cyanide was added and the solution was heated up to 80 to 95° C. At this reaction temperature, the solution was aerated for 5 h (alkaline heat treatment). Afterwards, the pH value was adjusted to a value of 2.5 to 3.5 using hydrochloric acid. Then, the solution was aerated at a temperature of 60 to 80° C. for 12 to 14 h (acid heat treatment). Finally, the solution was cooled down to a temperature of 20 to 30° C. and adjusted to a concentration of modified hydroxyethyl starch of 16.0 to 20.0° Bx.

Example 2

Complexation and Complex Stabilization

To form an iron HES complex, iron(III) chloride was added to the modified hydroxyethyl starch of example 1 (any other heptonic-acid modified hydroxyethyl starch could also have been used). In doing so, an iron(III) chloride solution having a concentration of around 40% (w/v) iron(III) chloride was used (iron content 190 to 210 mg/ml). The ratio of iron to modified hydroxyethyl starch was approximately 1:2.7 (kg/kg). Within 24 to 36 h, a 20% sodium carbonate solution was added to this solution of iron(III) chloride and modified hydroxyethyl starch, until a pH value of 2.5 to 3.5 was again reached. Then, the complex was stabilized by a three-step temperature-time program and pH adjustment.

For performing the first heat treatment, the solution was heated up to a temperature of 80 to 95° C. and stirred for 1 h. After cooling the solution down to a temperature of 20 to 30° C., the pH value was adjusted to a value of 3.5 to 4.5.

For the second heat treatment, the solution was again heated up to a temperature of 80 to 95° C., stirred for 1 h and once again cooled down to a temperature of 20 to 30° C. Then, the pH value was adjusted to a value of 4.6 to 5.5.

For the third heat treatment, the solution was once again heated up to a temperature of 80 to 95° C., stirred for 1 h, cooled down to a temperature of 20 to 30° C. Then, the pH value was adjusted to a value of 5.6 to 6.5.

By those three subsequent heat treatments, a complex stabilization took place due to which the iron ions were very well stabilized in the modified hydroxyethyl starch, but could be released afterwards within an organism after an according uptake.

The iron HES complex formed in this example had an iron content of 5.04% (w/v), i.e. the iron concentration was 5.04 g iron per 100 ml solution.

Example 3

Finishing

For finishing, the solution obtained by performing example 2 was pre-filtered through a pre-filter layer. After this pre-filtration, an ultrafiltration took place. During this ultrafiltration, small molecules like dissolved salts and fragments with a low molecular weight were removed. This ultra filtration was carried out as diafiltration, using water for injection as solvent. It was stopped after the filtrate has reached a conductivity of less than 3 mS/cm. Then, the solution was concentrated until the desired iron content was reached.

Finally, the iron content was once again adjusted to the desired iron concentration using water for injection as dilution medium. Furthermore, the pH value of the solution was adjusted to the target value by sodium hydroxide or hydrochloric acid. To characterize the solution formed, the viscosity, the density and the hydroxyethyl starch content were controlled.

After these adjustments, the solution was filtered through a filter cascade of pre-filter layer and a secondary filter cartridge. The solution was then drawn off in labelled canisters for further use.

The final solution had a dark brown colour, a viscosity 7.2 $mm^2/s$, a density of 1.090 g/ml, a pH value of 5.1, a cyanide concentration of 0.080 ppm, a free iron content of 0.056 g/100 ml, a chloride content of 0.280 g/ml, an iron content of 5.04 g/100 ml, an HES content of 8.93 g/100 ml and a dry matter content of 12.26 g/100 ml.

Example 4

Free Iron Content

Free iron has the potential to generate reactive oxygen species. Therefore, the free iron content of an iron complex to be administered to an individual should be as low as possible. Thus, the free iron content is a measure of the quality of the iron complex in terms of its suitability to be used as active ingredient for a medicinal product or medicament.

The free iron content of the iron HES complex produced in examples 1 to 3 was determined and compared to the free iron content of other iron complexes present on the market. These other iron complexes are an iron dextran (marketed under the name CosmoFer) having an iron concentration of 50 g/l, an iron sucrose (marketed under the name Venofer) having an iron concentration of 20 g/l and an iron gluconate (marketed under the name Ferrlecit) having an iron concentration of 12.5 g/l.

For determining the free iron content, a spectrometric analysis using a UV/VIS spectrophotometer was done. The extinction of calibration solutions and the respective sample solutions was measured at a wave length of 533 nm using a 10-mm measuring cell.

The calibration solutions were in each case solutions of 5.0 ml hydroxylamine hydrochloride solution (20% (w/v)), 10.0 ml bathophenanthroline solution (33.2% (w/v)), 5.0 ml sodium acetate solution (10% (w/v)) and 10 ml iron solution (x ml 0.001% (w(v)) iron(III) nitrate in 0.005 mol nitric acid plus (10.0−x) ml water, wherein x was 2.0, 3.0, 4.0, 5.0, 6.0 and 7.0). Prior to use, the solutions were extracted for three times with 10 ml chloroform each time. The chloroform extracts (lower layers) were filled up with isopropanol to 100 ml.

The sample solutions were in each case solutions of 5.0 ml hydroxylamine hydrochloride solution (20% (w/v)), 10.0 ml bathophenanthroline solution (33.2% (w/v)), 5.0 ml sodium acetate solution (10% (w/v)), 2 ml sample and 498 ml water. Prior to use, the solutions were extracted for three times with 10 ml chloroform each time. The chloroform extracts (lower layers) were filled up with isopropanol to 100 ml.

The extinction of the calibration solutions and the test solution were determined by using isopropanol as blank.

The measured extinctions of the calibration solutions were used to calculate a regression line and the corresponding regression equation. The concentration of iron in the sample solutions was determined using the regression equation.

The results are depicted in FIG. 1. The content of free iron was 1.19% (w/v) in case of the iron dextran, 2.12% (w/v) in case of the iron sucrose, 1.41% (w/v) in case of the iron gluconate and only 0.24% (w/v) in case of iron HES.

Thus, iron HES produced by a method according to an aspect of the invention shows a significantly better complex stability and lower content of free iron than other iron compounds being presently on the market. Therefore, the modified hydroxyethyl starch as described herein above is a valuable basic product for an according iron HES complex. This iron HES complex in turn is a compound of particular interest for medical applications in humans or animals.

The claimed manufacturing method cannot be compared with manufacturing methods disclosed in prior art relating to different starting materials. To give an example, manufacturing methods with dextrans or dextrins as starting material make use of completely different method steps since the chemistry of dextrans and dextrins on the one hand and hydroxyethyl starch on the other hand is quite different although the chemical structures of the substances appears to be similar. Technical details obtained from manufacturing methods using different starting materials cannot be transferred to the instantly claimed method.

What is claimed is:

1. A method for manufacturing a hydroxyethyl starch carrying a heptonic acid residue on at least one of its termini, comprising the following steps:
   a) dissolving hydroxyethyl starch in water,
   b) adjusting the pH value to a value of 8.0 to 10.0,
   c) adding a cyanide compound to the hydroxyethyl starch solution, heating the solution to a temperature of 80 to 99° C. and keeping it at this temperature for a first time period, and
   d) adjusting the pH value to a value of 2.0 to 4.0, bringing the solution to a temperature of 50 to 90° C. and keeping it at this temperature for a second time period.

2. The method according to claim 1, wherein the hydroxyethyl starch has a weight average molecular weight of less than 200 000 g/mol.

3. The method according to claim 1, wherein the hydroxyethyl starch has an average degree of molar substitution of 0.4 to 0.6.

4. The method according to claim 1, wherein the hydroxyethyl starch is made from potato starch.

5. The method according to claim 1, wherein step d) is followed by the following steps:

e) cooling down the solution to a temperature of 10 to 40° C.,
   f) adding an iron compound to the solution,
   g) after a third time period, adjusting the pH value of the solution to a value of 2.0 to 4.0, and
   h) stabilizing the formed hydroxyethyl starch complex by at least once heating it to a temperature of 80 to 99° C., cooling it down to a temperature of 10 to 40° C. and adjusting the pH value to a value of 3.0 to 7.0.

6. The method according to claim 5, wherein step h) is carried out in such a way that the pH value obtained after a heating step succeeding a previous heating step is higher than the pH value in the previous heating step.

7. The method according to claim 5, wherein step h) is carried out by the following sub-steps:
   h1) heating the solution to a temperature of 80 to 99° C., keeping it at this temperature for a forth time period, cooling it down to a temperature of 10 to 40° C., adjusting the pH value to a value of 3.0 to 5.0,
   h2) heating the solution to a temperature of 80 to 99° C., keeping it at this temperature for a fifth time period, cooling it down to a temperature of 10 to 40° C., adjusting the pH value to a value of 4.0 to 6.0, and
   h3) heating the solution to a temperature of 80 to 99° C., keeping it at this temperature for a sixth time period, cooling it down to a temperature of 10 to 40° C., adjusting the pH value to a value of 5.0 to 7.0.

8. The method according to claim 5, wherein the iron compound is an iron salt.

9. The method according to claim 8, wherein the iron salt is an iron(III) salt.

10. The method according to claim 5, wherein the complex of hydroxyethyl starch and iron has a radius of gyration in the range of 30 to 70 nm.

11. The method according to claim 1, wherein the hydroxyethyl starch has a weight average molecular weight of less than 130 000 g/mol.

12. The method according to claim 1, wherein the hydroxyethyl starch has a weight average molecular weight of less than 100 000 g/mol.

13. The method according to claim 1, wherein the hydroxyethyl starch has a weight average molecular weight of less than 90 000 g/mol.

14. The method according to claim 1, wherein the hydroxyethyl starch has a weight average molecular weight of less than 85 000 g/mol.

15. The method according to claim 1, wherein the hydroxyethyl starch has a weight average molecular weight of less than 80 000 g/mol.

16. The method according to claim 1, wherein the hydroxyethyl starch has a weight average molecular weight of less than 75 000 g/mol.

17. The method according to claim 1, wherein the hydroxyethyl starch has an average degree of molar substitution of 0.45 to 0.55.

18. The method according to claim 5, wherein the complex of hydroxyethyl starch and iron has a radius of gyration in the range of 40 to 60 nm.

19. The method according to claim 5, wherein the complex of hydroxyethyl starch and iron has a radius of gyration in the range of 45 to 55 nm.

* * * * *